(12) United States Patent
Umebayashi

(10) Patent No.: US 7,771,407 B2
(45) Date of Patent: Aug. 10, 2010

(54) METHOD OF PRODUCING DISPOSABLE PANTS HAVING DISCONTINUOUS ELASTIC ELEMENTS

(75) Inventor: Toyoshi Umebayashi, Osaka (JP)

(73) Assignee: Zuiko Corporation, Osaka (JP)

(*) Notice: Subject to any disclaimer, the term of this patent is extended or adjusted under 35 U.S.C. 154(b) by 1783 days.

(21) Appl. No.: 10/365,195

(22) Filed: Feb. 11, 2003

(65) Prior Publication Data
US 2003/0135189 A1 Jul. 17, 2003

Related U.S. Application Data

(62) Division of application No. 09/937,428, filed as application No. PCT/JP00/02889 on May 2, 2000, now Pat. No. 6,554,815.

(30) Foreign Application Priority Data
Jun. 16, 1999 (JP) ................. 11-169765

(51) Int. Cl.
 *A61F 13/15* (2006.01)
 *B29C 65/00* (2006.01)
 *C09J 5/00* (2006.01)
(52) U.S. Cl. ............... 604/385.22; 604/385.26; 604/385.27; 604/385.31; 156/308.4; 156/311; 156/580.1
(58) Field of Classification Search ............ 604/385.22, 604/385.26, 385.27, 385.31; 156/308.4, 156/311, 580.1
See application file for complete search history.

(56) References Cited

U.S. PATENT DOCUMENTS

| 4,795,510 | A | 1/1989 | Wittrock et al. |
| 5,624,424 | A * | 4/1997 | Saisaka et al. ......... 604/385.28 |
| 5,858,012 | A | 1/1999 | Yamaki et al. |
| 6,210,386 | B1 | 4/2001 | Inoue |
| 6,306,122 | B1 | 10/2001 | Narawa et al. |
| 6,312,420 | B1 | 11/2001 | Sasaki et al. |
| 6,369,291 | B1 | 4/2002 | Uchimoto et al. |
| 6,391,013 | B1 | 5/2002 | Suzuki et al. |

FOREIGN PATENT DOCUMENTS

JP         10-277091        10/1998

* cited by examiner

*Primary Examiner*—Jacqueline F. Stephens
(74) *Attorney, Agent, or Firm*—Renner, Otto, Boisselle & Sklar, LLP

(57) ABSTRACT

A method of producing disposable under-shorts having a fit gather laminate at high speeds. The method includes disposing an elastic member (1) between a pair of upper and lower non-woven fabric sheets (6, 7) in the width direction, intermittently securing the elastic member (1) to portions of the non-woven fabric sheets (6, 7) and cutting a non-secured section of the elastic member (1). The method also may include cutting the fabric sheets into pieces of a predetermined size and shape, folding the pieces along a center line, attaching together the left edges and attaching together the right edges to form a fit gather laminate. The method may further comprise attaching a reinforcing sheet (3) to the under-side of the fit gather laminate (2), and disposing an absorber (4) on the upper-side of the laminate (2), and a back sheet (5) on the under-side of the reinforcing sheet (3).

5 Claims, 5 Drawing Sheets

METHOD OF PRODUCING DISPOSABLE PANTS HAVING DISCONTINUOUS ELASTIC ELEMENTS

This is a divisional of U.S. patent application Ser. No. 09/937,428 filed on Jan. 11, 2002, now U.S. Pat. No. 6,554,815 which is a national stage application of International Patent Application No. PCT/JP00/02889, filed May 2, 2000, both of which are hereby incorporated herein by reference in their entirety. The International Patent Application was not published in the English language.

TECHNICAL FIELD

The present invention relates to disposable pants having a fit gather laminate in which an elastic member is provided between a pair of upper and lower non-woven fabric sheets, and a method of manufacturing the same.

BACKGROUND ART

As described in Japanese Laid-Open Patent Publication No. 6-197920, for example, a method known in the prior art of manufacturing a briefs type body fluid absorbing article, including the steps of: transferring a back sheet having waist gathers in the longitudinal direction while folding the back sheet downward at a predetermined interval, supplying a waist side elastic body in the longitudinal direction on the upper surface of the back sheet being transferred, supplying a holding non-woven fabric in the longitudinal direction on the upper surface thereof, and bonding the waist side elastic body and the holding non-woven fabric on the back sheet except for the downward folded portions; cutting off the waist side elastic body and the holding non-woven fabric integrated with the back sheet along the top edge of each downward folded portion of the back sheet, and then unfolding the downward folded portions to make the back sheet back into a sheet form, thereby forming a back sheet having the waist side elastic bodies at a predetermined interval; bonding a body fluid absorbent to areas of the back sheet after the previous step where the waist side elastic body does not exist; cutting out leg hole openings in the back sheet after the previous step, and then dividing the back sheet by cutting it off along the center line of the leg hole opening into individual intermediate products; and folding in two each intermediate product with the waist side elastic body and the body fluid absorbent being located inside, and bonding together the waist side sections.

The method of manufacturing a body fluid absorbing article described in the above-identified publication provides the following advantage: the waist side elastic body is provided in the left-right direction except for the widthwise center area and the longitudinal center area of the body fluid absorbent, thereby reducing the area on which the waist side elastic body is provided and thus reducing the material cost; the waist side elastic body is supplied in the direction in which the back sheet is transferred, thereby increasing the speed of the production line; and it is possible to obtain a body fluid absorbing article that can be easily worn by stretching the waist side elastic body, and that provides an improved fit to the body without giving a feeling of excessive pressure to the wearer.

However, in the case where the operation of transferring a back sheet having waist gathers in the longitudinal direction while folding the back sheet downward at a predetermined interval and supplying a waist side elastic body and a holding non-woven fabric on the upper surface of the back sheet, the operation of bonding the waist side elastic body and the holding non-woven fabric on the back sheet except for the downward folded portions, and the operation of cutting off the waist side elastic body and the holding non-woven fabric integrated with the back sheet along the top edge of each downward folded portion of the back sheet, are performed, the operation speed needs to be reduced since these operations are difficult to perform, and it is necessary to provide a folding mechanism for folding the back sheet downward, thereby complicating the structure of the manufacturing apparatus.

The present invention has been made in view of the above, and has an object to realize a high-speed manufacture of disposable pants having a fit gather laminate in which an elastic member is provided between a pair of upper and lower non-woven fabric sheets, without complicating the structure of the manufacturing apparatus.

DISCLOSURE OF THE INVENTION

Disposable pants of the present invention include: a fit gather laminate in which an elastic member is provided between a pair of upper and lower non-woven fabric sheets in a widthwise direction thereof, with the elastic member being secured on areas of the non-woven fabric sheets except for a widthwise center area thereof and being cut off along the widthwise center area of the non-woven fabric sheets; a reinforcement sheet secured on a lower surface side of the fit gather laminate in the widthwise center area thereof; an absorbent provided on an upper surface side of the fit gather laminate; and a back sheet provided on a lower surface side of the reinforcement sheet.

With the structure described above, the elastic members are provided in areas of the non-woven fabric sheets forming the fit gather laminate except for the widthwise center area thereof and the elastic members are allowed to shrink/stretch, whereby they can be securely worn, while the shrinking/stretching force of the elastic members is prevented from acting upon the widthwise center area of the fit gather laminate, where the absorbent is provided, thereby forming the area where the absorbent is provided in a flat shape. Moreover, the reinforcement sheet is secured on the lower surface side of the fit gather laminate in the widthwise center area thereof, whereby areas where the elastic members are cut off are reinforced by the reinforcement sheet.

A method of manufacturing disposable pants of the present invention includes: transferring continuous materials of a pair of non-woven fabric sheets forming a fit gather laminate and a continuous material of an elastic member provided therebetween in a longitudinal direction thereof while intermittently securing the continuous material of the elastic member on the non-woven fabric sheets; cutting off the elastic member along with the non-woven fabric sheets along a non-secured area thereof; securing a reinforcement sheet on a lower surface side of the fit gather laminate at a position corresponding to the non-secured area of the elastic member while providing an absorbent on an upper surface side of the fit gather laminate; and providing a back sheet on a lower surface side of the reinforcement sheet.

With the structure described above, the elastic members are provided in areas except for the widthwise center area and the areas are allowed to shrink/stretch, while the shrinking/stretching force of the elastic members is prevented from acting upon the widthwise center area, where the absorbent is provided. Moreover, the reinforcement sheet is secured on the lower surface side in the widthwise center area. Therefore, disposable pants having the fit gather laminate in which areas where the elastic members are cut off are reinforced by the reinforcement sheet can be manufactured at a high speed using a manufacturing apparatus having a simple structure.

BEST MODE FOR CARRYING OUT THE INVENTION

Figure 1:
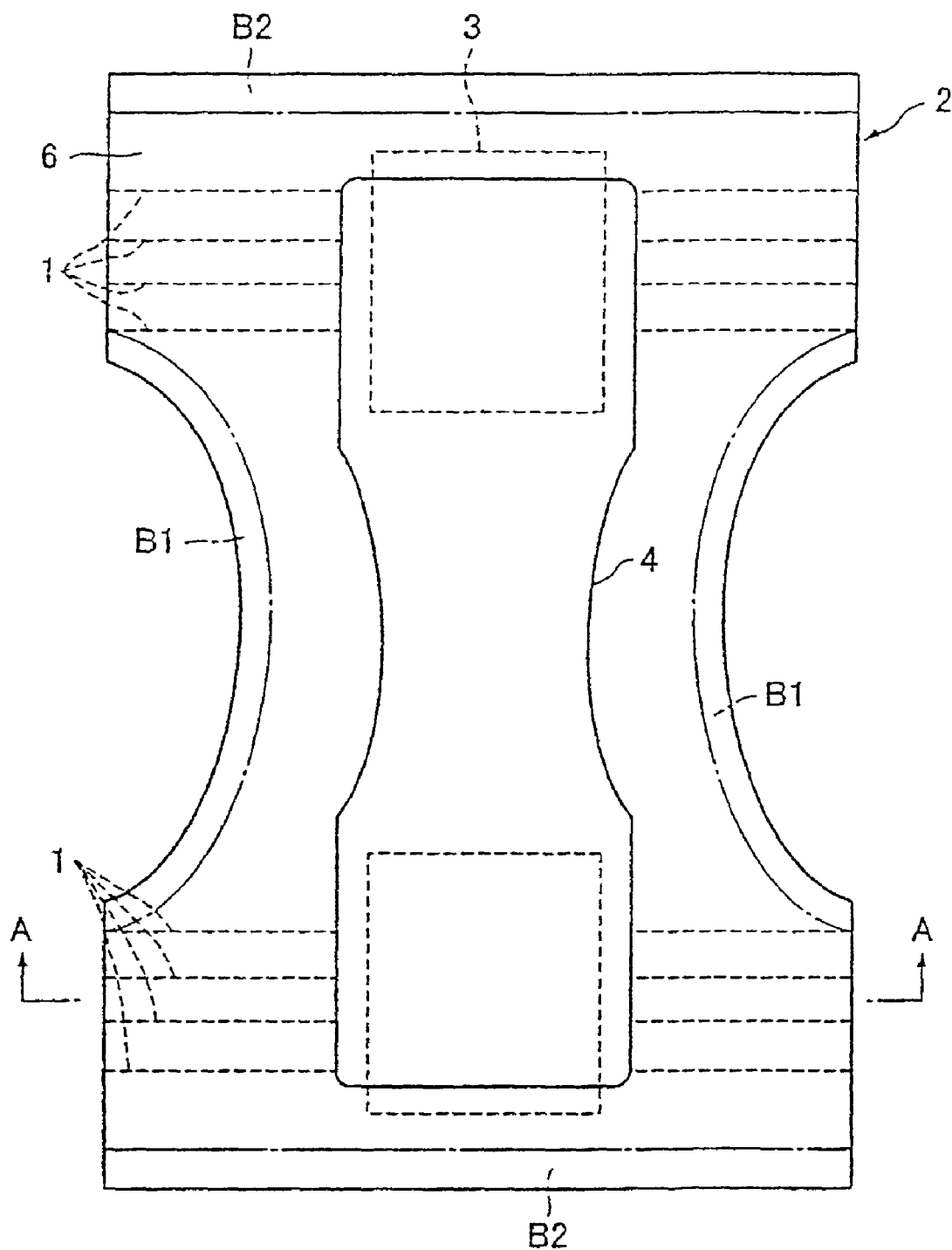
FIG. 1 is a diagram illustrating disposable pants according to an embodiment of the present invention in an unfolded state.
Figure 2:
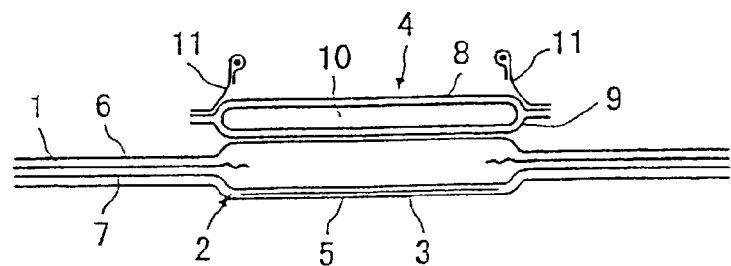
FIG. 2 is a cross-sectional view taken along line A-A of FIG. 1.

FIG. 1 and FIG. 2 illustrate a disposable pants material obtained by unfolding disposable pants according to an embodiment of the present invention. The disposable pants material includes: a fit gather laminate 2 having a plurality of elastic members 1 extending in the widthwise direction in areas of the fit gather laminate 2 except for the widthwise center area; a pair of front and back reinforcement sheets 3 secured on the lower surface side of the fit gather laminate 2, i.e., the outer surface side of the disposable pants, in the widthwise center area of the fit gather laminate 2; an absorbent 4 provided on the upper surface side of the fit gather laminate 2, i.e., the inner surface side of the disposable pants located on the body contact surface side; and a back sheet 5 provided on the lower surface side of the reinforcement sheets 3.

The elastic member 1 is made of a linear or band-like rubber material, a material under the trade name "Operon" from Du Pont-Toray Co., Ltd., or the like, and is provided, while being stretched, between the pair of upper and lower non-woven sheets 6 and 7 to be secured on areas of the non-woven sheets 6 and 7 except for the widthwise center area thereof. The elastic member 1 is cut off in the widthwise center area of the non-woven sheets 6 and 7 so that a shrinking/stretching force of the elastic members 1 does not act upon the widthwise center area.

The non-woven sheets 6 and 7 are each formed in an hourglass shape using a flexible material such as a polypropylene, a polyethylene, a polyester or a rayon. The upper non-woven sheet 6 and the lower non-woven sheet 7 are bonded together by an adhesive such as a hot melt in the area where the elastic members 1 are provided, with the elastic members 1 being provided in areas except for the widthwise center area, thus forming the fit gather laminate 2.

The reinforcement sheet 3 is made of a plastic film material, or the like, having an appropriate rigidity, and is secured on the lower surface side of the fit gather laminate 2 in the widthwise center area thereof. On the lower surface side of the reinforcement sheet 3, i.e., on the outer surface side of the disposable pants, a character design or a character, etc., is printed as necessary (see FIG. 3).

As illustrated in FIG. 2, the absorbent 4 includes an upper liquid-permeable sheet 8 made of a non-woven fabric, a plastic film material having holes therein, or the like, a lower liquid-impermeable sheet 9 made of a plastic film material, or the like, and an absorption mat 10 provided between the sheets 8 and 9 and made of crushed pulp, a highly water-absorbing resin, a shape-retaining thermoplastic resin, or the like. It is preferred to provide, on the upper surface of the liquid-permeable sheet 8 along the left and right edges thereof, a pair of left and right raised gathers 11 having an elastic member made of a linear rubber material, or the like, attached in the longitudinal direction of the disposable pants.

The back sheet 5 is made of a flexible material such as a polypropylene, a polyethylene, a polyester or a rayon, is provided so as to cover the entire lower surface of the fit gather laminate 2 on the lower surface side of the reinforcement sheet 3, and is bonded on the lower surface of the fit gather laminate 2 by an adhesive such as a hot melt.

Figure 3:
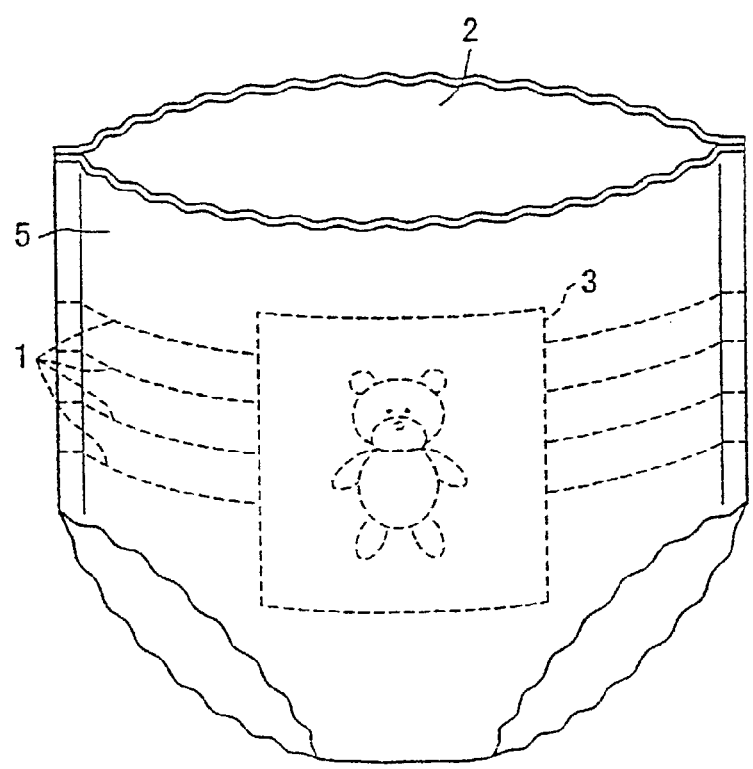
FIG. 3 is a diagram illustrating an embodiment of disposable pants according to the present invention.

Then, the disposable pants material having the fit gather laminate 2 and the back sheet 5 is folded in two along the longitudinal center area thereof, and the left and right edges of the fit gather laminate 2 are attached together by means of welding using an ultrasonic sealer or a heat sealer, or bonding using an adhesive, or the like, so as to form the material into a pants shape as illustrated in FIG. 3.

Figure 4:
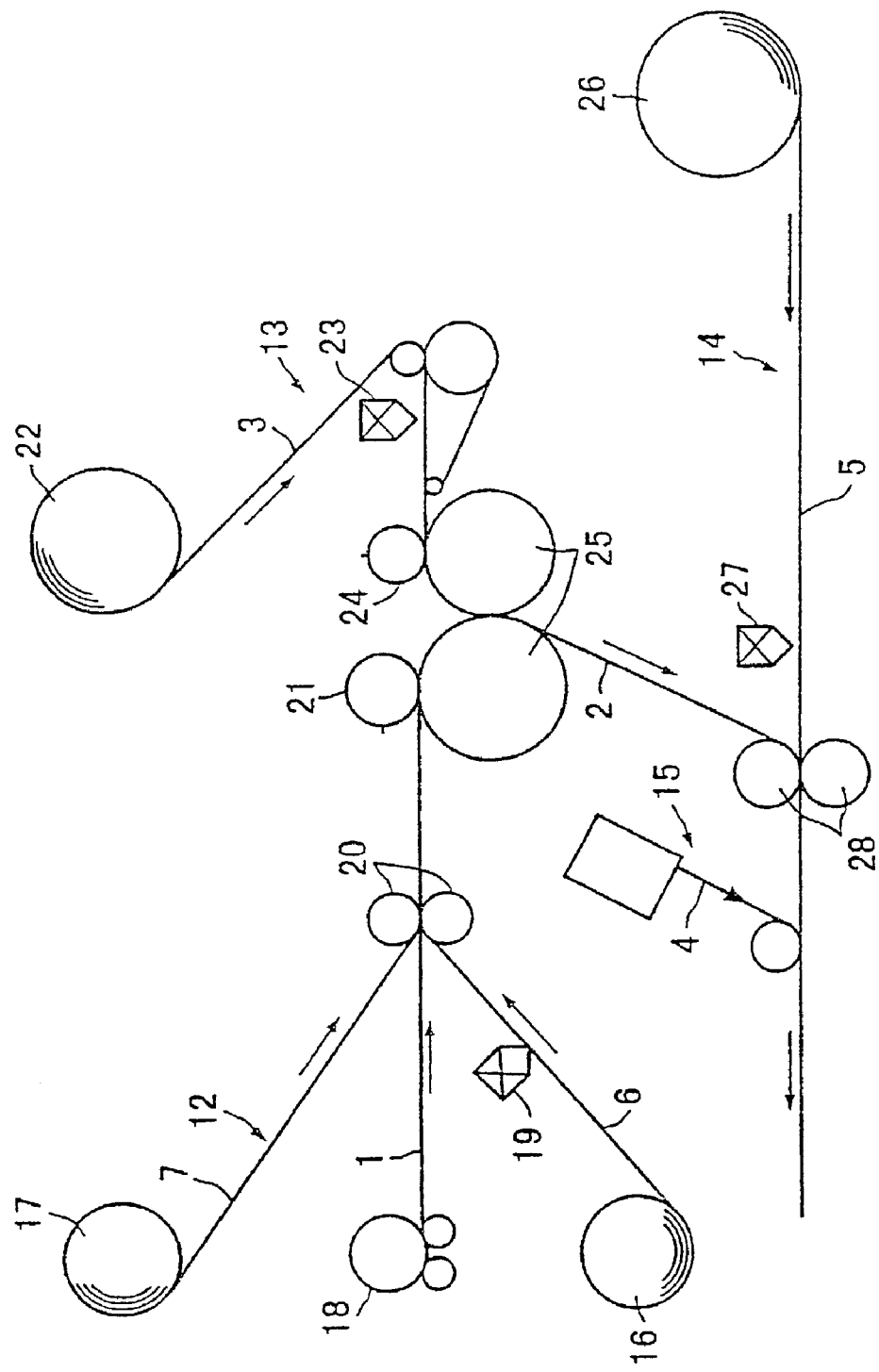
FIG. 4 is a diagram illustrating a specific example of a disposable pants manufacturing apparatus.

FIG. 4 illustrates the disposable pants manufacturing apparatus. The manufacturing apparatus includes a fit gather forming section 12 for forming a continuous material of the fit gather laminate 2, a reinforcement sheet bonding section 13 for bonding the reinforcement sheet 3 to the continuous material of the fit gather laminate 2, a back sheet bonding section 14 for bonding the back sheet 5 to the continuous material of the fit gather laminate 2, and an absorbent supply section 15 for supplying the absorbent 4 on the continuous material of the fit gather laminate 2.

The fit gather forming section 12 includes a pair of non-woven fabric rolls 16 and 17 for feeding the pair of non-woven sheets 6 and 7, respectively, an elastic member roll 18 for feeding the elastic members 1, a first hot melt applicator 19 for intermittently applying a hot melt on the non-woven sheet 6, a pressing roller 20 for pressing together the non-woven sheets 6 and 7, and a cutting roller 21 for cutting off the elastic members 1 along with the non-woven sheets 6 and 7 in areas where the hot melt is not applied.

The cutting roller 21 includes a plurality of cutting blades arranged at a predetermined interval so as to avoid unnecessarily cutting off areas as much as possible while reliably cutting off the plurality of elastic members 1 between the non-woven sheets 6 and 7, and the cutting roller 21 is configured so as to intermittently cut off the non-woven sheets 6 and 7 having the elastic member 1.

The reinforcement sheet bonding section 13 includes a reinforcement sheet roll 22 for feeding a continuous material of the reinforcement sheet 3, a second hot melt applicator 23 for applying a hot melt on the continuous material of the reinforcement sheet 3 being fed from the reinforcement sheet roll 22, a cutting roller 24 for cutting off the continuous material of the reinforcement sheet 3 into pieces of a predetermined length, and a pressing roller 25 for pressing and bonding the reinforcement sheet 3, obtained by cutting off the continuous material, onto the lower surface side of the fit gather laminate 2.

The back sheet bonding section 14 includes a back sheet roll 26 for feeding a continuous material of the back sheet 5, a third hot melt applicator 27 for applying a hot melt on the continuous material of the back sheet 5 being fed from the back sheet roll 26, and a pressing roller 28 for pressing and bonding the continuous material of the back sheet 5 onto the lower surface side of the fit gather laminate 2.

The absorbent supply section 15 is configured so as to place the absorbent 4, produced in a separate step, on the fit gather laminate 2 while it is positioned at a predetermined position, and to secure the absorbent 4 on the upper surface side of the fit gather laminate 2 by means of welding using an ultrasonic sealer or a heat sealer, or bonding using an adhesive, or the like.

Figure 5:
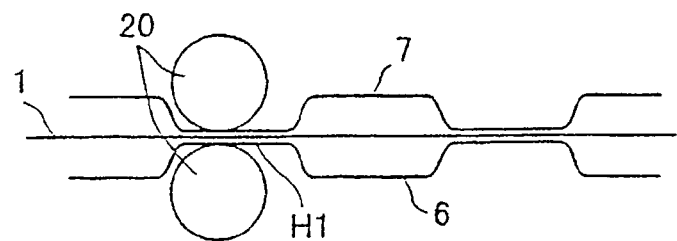
FIG. 5 is a diagram illustrating elastic members being secured on a non-woven sheet intermittently.

Disposable pants are manufactured as follows by using the manufacturing apparatus described above. The continuous materials of the pair of non-woven sheets 6 and 7 being fed from the non-woven fabric rolls 16 and 17 are transferred in the longitudinal direction thereof while the elastic members 1 being fed from the elastic member roll 18 are placed therebetween. Then, after a hot melt is applied by the first hot melt applicator 19 intermittently at a predetermined interval on the non-woven sheet 6, the non-woven sheets 6 and 7 are sandwiched and pressed together by the pressing roller 20, thereby bonding together the non-woven sheets 6 and 7 and the elastic members 1 in areas where the hot melt H1 is applied, as illustrated in FIG. 5.

Figure 6:
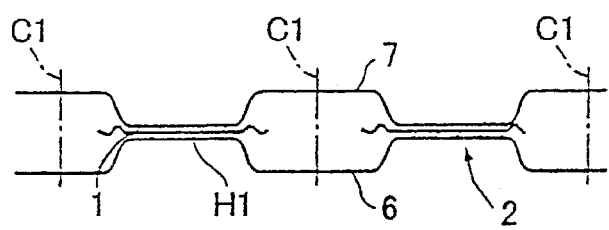
FIG. 6 is a diagram illustrating the elastic members being broken off.
Figure 7:
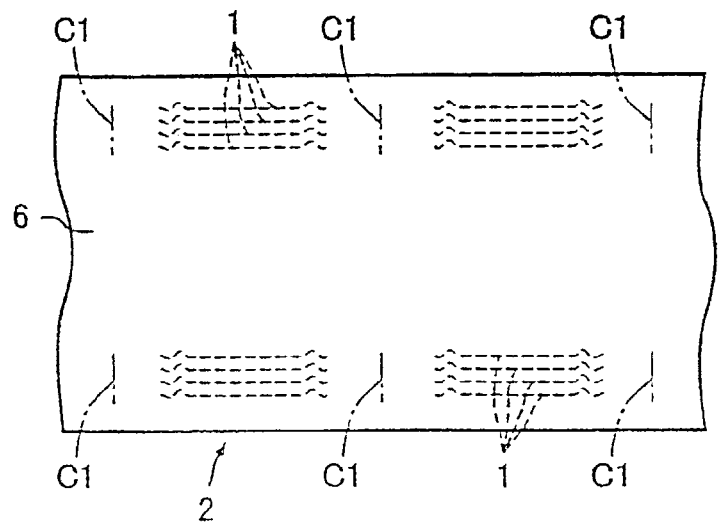
FIG. 7 is a diagram illustrating the elastic members being broken off, as viewed in a plan view.

Then, by using the cutting roller 21, the continuous materials of the elastic members 1, along with the continuous materials of the non-woven sheets 6 and 7, are cut off along a cut-off line C1 in non-adhesive areas as illustrated in FIG. 6 and FIG. 7, thereby forming a continuous material of the fit gather laminate 2 in which the elastic members 1 having a predetermined length are placed between the non-woven sheets 6 and 7 being stretched, while secured on the non-woven sheets 6 and 7.

Figure 8:
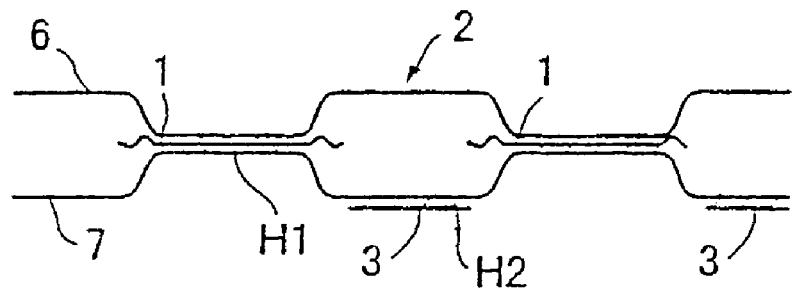
FIG. 8 is a diagram illustrating a fit gather laminate with a reinforcement tape being secured thereon.

Then, the reinforcement sheet 3 (obtained by applying a hot melt by the second hot melt applicator 23 on the upper surface side of the continuous material of the reinforcement sheet 3 being fed from the reinforcement sheet roll 22 and cutting off the continuous material of the reinforcement sheet 3 by the cutting roller 24 into pieces of a predetermined length) and the continuous material of the fit gather laminate 2 are sandwiched and pressed together by the pressing roller 25, whereby the reinforcement sheet 3 is bonded by a hot melt H2 on the lower surface side of the continuous material of the fit gather laminate 2 at positions corresponding to areas where the elastic members 1 are not provided, as illustrated in FIG. 8.

Then, after a hot melt is applied by the third hot melt applicator 27 on the upper surface side of the continuous material of the back sheet 5 being fed from the back sheet roll 26, the continuous material of the back sheet 5 and the continuous material of the fit gather laminate 2 are sandwiched by the pressing roller 28 so as to bond the continuous material of the back sheet 5 on the lower surface side of the reinforcement sheet 3.

Figure 9:
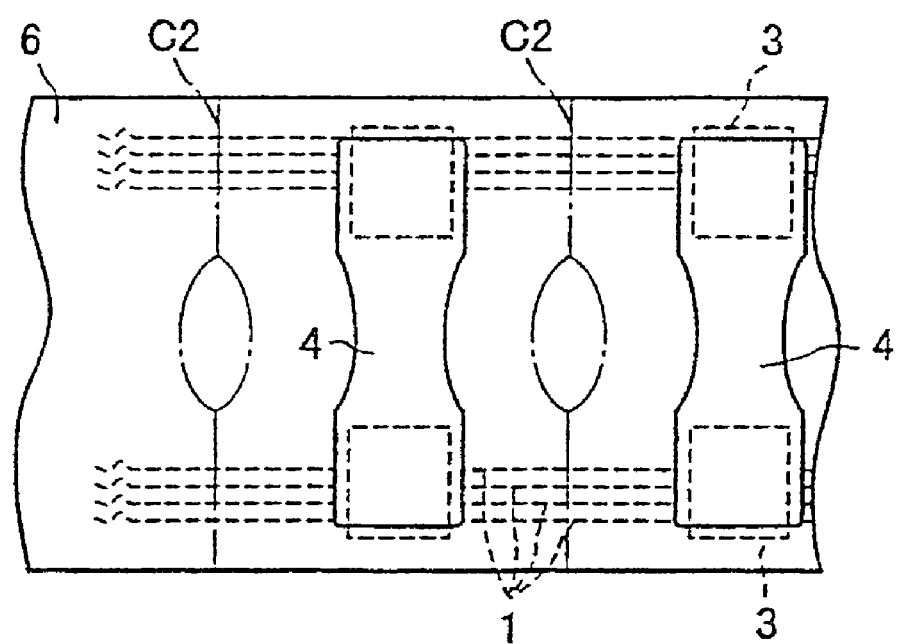
FIG. 9 is a diagram illustrating the structure of a continuous material of disposable pants.

Then, after the absorbent 4 supplied from the absorbent supply section 15 is placed on the upper surface side of the fit gather laminate 2, the absorbent 4 is bonded, for example, on the upper surface side of the continuous material of the fit gather laminate 2 while it is positioned at positions corresponding to areas where the elastic members 1 are not bonded, thereby forming a continuous material of a disposable pants material as illustrated in FIG. 9.

The disposable pants material illustrated in FIG. 1 is obtained by cutting off the thus formed continuous material of the disposable pants material along a cut-off line C2 into pieces having a predetermined size, and disposable pants illustrated in FIG. 3 can be manufactured by folding in two the disposable pants material along the longitudinal center area thereof and by attaching together the left and right edges of the fit gather laminate 2 by means of welding, bonding, or the like.

As described above, the disposable pants according to the present invention include the fit gather laminate 2 (in which the elastic members 1 are provided between the non-woven sheets 6 and 7 and secured on areas of the non-woven sheets 6 and 7 except for the widthwise center area thereof, and the elastic members 1 are cut off in the widthwise center area of the non-woven sheets 6 and 7), the reinforcement sheet 3 secured on the lower surface side of the fit gather laminate 2 in the widthwise center area thereof, the absorbent 4 provided on the upper surface side of the fit gather laminate 2, and the back sheet 5 provided on the lower surface side of the reinforcement sheet 3. Therefore, the elastic members 1 provided in areas of the non-woven sheets 6 and 7 forming the fit gather laminate 2 except for the widthwise center area thereof are allowed to shrink/stretch, whereby they can be securely worn while effectively preventing the occurrence of leakage of fluid, etc.

Moreover, since the elastic members 1 are not provided in the widthwise center area of the fit gather laminate 2 where the absorbent 4 is provided, it is possible to prevent the area where the absorbent 4 is provided from being deformed due to the influence of the shrinking/stretching force of the elastic members 1. Therefore, it is possible to realize a good appearance and a stable wearing feeling, while preventing wrinkles from being formed in the widthwise center area of the disposable pants where the absorbent 4 is provided.

The reinforcement sheet 3 is secured on the lower surface side of the fit gather laminate 2 in the widthwise center area thereof, whereby even when the elastic members 1 are cut off along with the non-woven sheets 6 and 7, the area where the elastic members 1 are cut off can be reinforced by the reinforcement sheet 3. Therefore, it is not required to perform complicated operations (such as placing and securing the elastic members 1, which have been cut off in advance into pieces having a predetermined length, between the non-woven sheets 6 and 7, or as illustrated in the conventional example, transferring a back sheet having waist gathers while folding the back sheet downward and cutting off the waist side elastic body and the holding non-woven fabric integrated with the back sheet along the top edge of each downward folded portion of the back sheet), and it is possible to manufacture, at a high speed and continuously, disposable pants in which the elastic members 1 are secured on areas of the non-woven sheets 6 and 7 except for the widthwise center area thereof.

Thus, as described above, the disposable pants can be produced at a high speed and continuously using a manufacturing apparatus having a simple structure by transferring the continuous materials of the pair of non-woven sheets 6 and 7 forming the fit gather laminate 2 and the continuous materials of the elastic members 1 therebetween in the longitudinal direction thereof while intermittently bonding the continuous materials of the elastic members 1 on the non-woven sheets 6 and 7, cutting off the elastic members 1 along with the non-woven sheets 6 and 7 along areas where the elastic members 1 are not secured, securing the reinforcement sheet 3 on the lower surface side of the fit gather laminate 2 at positions corresponding to areas where the elastic members 1 are not secured, providing the absorbent 4 on the upper surface side thereof, and providing the back sheet 5 on the lower surface side of the reinforcement sheet 3.

Moreover, in the case where the back sheet 5 is provided on the lower surface side of the reinforcement sheet 3, as described above, so that substantially the entirety of the outer surface of the disposable pants is covered by the back sheet 5, it is possible to avoid the awkwardness due to the coexistence of a plurality of materials on the outer surface side of the disposable pants, thereby effectively improving the appearance.

Moreover, in the case where a character design or a character, etc., is printed on the lower surface side of the reinforcement sheet 3, as illustrated in the embodiment described above, the character design, etc., can be seen through the semitransparent back sheet 5 made of a non-woven fabric sheet, or the like, whereby it is possible to effectively improve the decorativeness of the disposable pants.

In order to further improve the close fitting property of the disposable pants onto the body, it is desirable to provide each of a leg hole section B1 located along each widthwise edge of the fit gather laminate 2 and a waist section B2 located along each longitudinal edge thereof with an elastic member made of a linear rubber material, or the like, as shown in phantom lines in FIG. 1.

Instead of the embodiment described above where the disposable pants material is folded in two along the longitudinal center area thereof and the left and right edges of the fit gather laminate 2 are attached together, the left and right edges may be detachably attached together with a holding member made of an adhesive tape, a mechanical planar fastener, or the like.

INDUSTRIAL APPLICABILITY

As described above, the present invention provides an advantage that it is possible with a manufacturing apparatus having a simple structure to manufacture, at a high speed and continuously, disposable pants, in which the elastic members provided in areas of non-woven fabric sheets forming a fit gather laminate except for the widthwise center area thereof are allowed to shrink/stretch, whereby they can be securely worn while preventing the shrinking/stretching force of the elastic members from acting upon the widthwise center area of the fit gather laminate, where the absorbent is provided, thereby preventing the deformation of the area where the absorbent is provided.

The invention claimed is:

1. A method of manufacturing disposable pants, comprising: transferring continuous materials of a pair of non-woven fabric sheets forming a fit gather laminate and a continuous material of an elastic member provided therebetween in a longitudinal direction thereof while intermittently securing the continuous material of the elastic member on the non-woven fabric sheets; and cutting off the elastic along a non-secured area thereof.

2. A method as set forth in claim 1, further comprising cutting off the continuous materials into pieces having a predetermined size, folding the pieces along a longitudinal center thereof, attaching together left edges of the fit gather laminate, and attaching together right edges of the fit gather laminate.

3. A method as set forth in claim 2, wherein attaching the edges includes at least one of welding using an ultrasonic sealer, bonding using an adhesive, and welding using a heat sealer.

4. A method as set forth in claim 1, further comprising securing a reinforcement sheet on a lower surface side of the fit gather laminate at a position corresponding to the non-secured area of the elastic member while providing an absorbent on an upper surface side of the fit gather laminate.

5. A method as set forth in claim 4, further comprising providing a back sheet on a lower surface side of the reinforcement sheet.

\* \* \* \* \*